United States Patent
Gao et al.

(10) Patent No.: US 9,226,942 B2
(45) Date of Patent: Jan. 5, 2016

(54) EXPANDING HEMATOPOIETIC STEM CELLS

(71) Applicants: Hong Gao, Downingtown, PA (US); Zhenglun Zhu, Newton, MA (US)

(72) Inventors: Hong Gao, Downingtown, PA (US); Zhenglun Zhu, Newton, MA (US)

(*) Notice: Subject to any disclaimer, the term of this patent is extended or adjusted under 35 U.S.C. 154(b) by 0 days.

(21) Appl. No.: 14/294,664

(22) Filed: Jun. 3, 2014

(65) Prior Publication Data
US 2014/0322178 A1    Oct. 30, 2014

Related U.S. Application Data

(62) Division of application No. 13/303,675, filed on Nov. 23, 2011, now Pat. No. 8,741,640.

(60) Provisional application No. 61/417,193, filed on Nov. 24, 2010.

(51) Int. Cl.
| | |
|---|---|
| *A61K 35/14* | (2015.01) |
| *A61K 35/28* | (2015.01) |
| *A61K 31/519* | (2006.01) |
| *A61K 31/52* | (2006.01) |
| *A61K 31/5377* | (2006.01) |
| *A61K 31/573* | (2006.01) |
| *C12N 5/0789* | (2010.01) |
| *C12N 15/113* | (2010.01) |
| *G01N 33/50* | (2006.01) |
| *G01N 33/68* | (2006.01) |
| *C12Q 1/68* | (2006.01) |
| *C12N 5/071* | (2010.01) |
| *C12N 5/02* | (2006.01) |
| *C12N 15/00* | (2006.01) |
| *C12N 5/07* | (2010.01) |
| *A61K 35/18* | (2015.01) |
| *A01N 1/02* | (2006.01) |

(52) U.S. Cl.
CPC .............. *A61K 35/28* (2013.01); *A61K 31/519* (2013.01); *A61K 31/52* (2013.01); *A61K 31/5377* (2013.01); *A61K 31/573* (2013.01); *C12N 5/0647* (2013.01); *C12N 15/113* (2013.01); *C12Q 1/6881* (2013.01); *G01N 33/5073* (2013.01); *G01N 33/5091* (2013.01); *G01N 33/6893* (2013.01); *C12N 2310/11* (2013.01); *C12N 2310/14* (2013.01); *C12N 2501/405* (2013.01); *C12N 2501/415* (2013.01); *C12N 2501/60* (2013.01); *G01N 2800/22* (2013.01)

(58) Field of Classification Search
None
See application file for complete search history.

(56) References Cited

U.S. PATENT DOCUMENTS

| 8,741,640 B2 * | 6/2014 | Gao et al. ................. 435/372 |
| 2006/0247193 A1 | 11/2006 | Taira et al. |
| 2008/0032927 A1 | 2/2008 | Zhu et al. |
| 2012/0183553 A1 | 7/2012 | Zhu et al. |

OTHER PUBLICATIONS

Arseni, et al., "Characterization of the proteins HPIP and VENTX2 as novel regulatory proteins of human hematopoiesis theses submitted for a Doctoral Degree in Human Biology at the Faculty of Medicine", Jan. 1, 2006.
Arseni, et al., "The vent-like homeobox gene VENTX2 is expressed in human hematopoietic progenitor cells and promotes human myeloid development in vitro and in vivo", Blood, American Society of Hematology, 49th Annual meeting of the American Society of Hematology, Atlanta (2007).
Deeg, "Transplant strategies for patients with myelodysplastic sysndromes" 13 Current Opinion in Hematology 61-66 (2006).
Gao, et al., "Down-regulation of homeobox gene Ventx promotes expansion of human bone marrow hematopoietic stem cells (HSC)" American Society of Hematology, 53rd Annual meeting and Exposition, Session 501, Poster 1, No. 1272, San Diego (2011).
Gao, et al., "VentX, a novel lymphoid-enhancing factor/T-Cell factor associated transcription repressor, is a putative tumor suppressor" 70(1) 202-211 (2009).
Lindfield, et al., "Drug Therapy in the Heart Transplant Recipient Part II: Immunosuppressive Drugs" 110 Circulation 3858-3865 (2004).
Rawat, et al., "The vent-like homeobox gene VENTX promotes human myeloid differentiation and is highly expressed in acute myeloid leukemia", PNAS, 107(39) 16946-16951 (2010).
Sun, et al., "Single Mismatched Expanded Cord Blood Transplant for the Treatment of Hematological Diseases", 110 Blood 4056 (2007).
Tabbara, et al., "Current Concepts in Allogeneic Hematopoietic Stem Cell Transplantation" 23 Anticancer Research 5055-5068 (2003).
Ui-Tei, et al., :Guidelines for the selection of highly effective siRNA sequences for mammalian and chick RNA interference, 32(3) Nucleic Acids Research 936-948 (2004).

* cited by examiner

*Primary Examiner* — Nancy J Leith
(74) *Attorney, Agent, or Firm* — Cesari and McKenna, LLP

(57) ABSTRACT

A method of expanding hematopoietic stem cells. Also disclosed is a method of diagnosing primary or secondary bone marrow failure syndrome. The invention further includes a method of treating primary or secondary bone marrow failure syndrome.

10 Claims, No Drawings

EXPANDING HEMATOPOIETIC STEM CELLS

RELATED APPLICATION

This application is a continuation of U.S. application Ser. No. 13/303,675, filed on Nov. 23, 2011, which claims priority of U.S. Provisional Application No. 61/417,193, filed on Nov. 24, 2010. The contents of the prior applications are incorporated herein by reference in their entirety.

BACKGROUND OF THE INVENTION

Hematopiesis involves proliferation of hematopoietic stem cells (HSCs) and their differentiation into progenitors (e.g., erythroprogenitor cells). HSCs give rise to mature cells of all lineages of blood and immune systems.

Over the course of several decades, multiple lineage specific transcriptional factors, such as GATA-1 and EKLF, have been shown to play critical roles in hematopoiesis/erythropoiesis. Yet, the cell-intrinsic factors that allow expansion of hematopoiesis and erythropoiesis remain not completely understood. It has been shown that over-expression of several cell-intrinsic factors, such as WNT3a, beta-catenin, and HOXB4, leads to significant expansion of HSCs in mice. However, their effects on expansion of human HSCs are limited.

The difficulty in expanding human HSCs ex vivo represents a major challenge in human HSC-based therapeutic applications, e.g., reconstitution of the hematopoietic system. There is a need to develop a method of effectively expanding human HSCs.

SUMMARY OF THE INVENTION

The present invention is based on an unexpected result that down-regulation of VentX leads to ex vivo expansion of human HSCs, which are CD34+, in both in vitro and in vivo.

One aspect of the invention is related to a method of expanding HSCs. The method includes two steps; (1) isolating HSCs from a subject (e.g., a human and a non-human mammal), and (2) contacting the HSCs with an agent that inhibits expression or activity of a VentX polypeptide, thereby increasing expansion of the HSCs. The isolating step can be performed by obtaining from the subject a biological sample containing HSCs (e.g., bone marrow, peripheral blood, and cord blood) and collecting HSCs from the biological sample.

In one example, the agent is an immunosuppressive agent, e.g., IMURAN® (azathioprine), methotrexate, prednisone, or CELLCEPT® (mycophenolic acid). The agent can also be an interfering RNA (iRNA) agent, an antisense oligonucleotide, a ribozyme, or an antibody.

The iRNA agent has a first strand having a first nucleotide sequence homologous to a region of a gene encoding VentX protein. The iRNA agent targets an mRNA transcribed from the gene, including its 5' un-translated area.

The first nucleotide sequence can be an RNA version, e.g.,

UUCAGAAUCGCCGCAUGAAACACAAACGG, (SEQ ID NO: 5)

UCUACUCAACGUCUUCUGGCCUUGCCAAU, (SEQ ID NO: 6)

CAAAUCUGCCUGCGCCGGAGAGGACCAUG, (SEQ ID NO: 7)

GGUUGAGUAAGGAGCCAAAUACCUUGCGG, (SEQ ID NO: 8)

CGGGUUGAGUAAGGAGCCAAAUA, (SEQ ID NO: 9)

CCGCAUGAAACACAAACGGCAAA, (SEQ ID NO: 10)

CCCCAGCUUUCUACUCAACGUCU, (SEQ ID NO: 11)

GGGUUGAGUAAGGAGCCAA, (SEQ ID NO: 29)

GGUUGAGUAAGGAGCCAAA, (SEQ ID NO: 30)

GCUCUCAGAGGUCCAGAUA, (SEQ ID NO: 31)

GGUUUCAGAAUCGCCGCAU, (SEQ ID NO: 32)

UCAGAAUCGCCGCAUGAAA, (SEQ ID NO: 33)

UCGCCGCAUGAAACACAAA, (SEQ ID NO: 34)

GCCGCAUGAAACACAAACG, (SEQ ID NO: 35)

GCAUGAAACACAAACGGCA, (SEQ ID NO: 36)

GCUUUCUACUCAACGUCUU, (SEQ ID NO: 37)

UCUCUGCCAAGUGGCACAA, (SEQ ID NO: 38)

GGACUCAGUUGUUCUGUUU, (SEQ ID NO: 39)

CCCGGCCCUGAGAAUAUAU, (SEQ ID NO: 40)

CCGGCCCUGAGAAUAUAUU, (SEQ ID NO: 41)

GGUCAGUGAACAGAGUCAA, (SEQ ID NO: 42)

GCAGAAGUGGGCUUGUCAU, (SEQ ID NO: 43)

GCAGGUGUGUUUAUAGCGU, (SEQ ID NO: 44)

GGAAAGCAGGAGGGAACAA, (SEQ ID NO: 45)

GCGUUGAUGGACCGUUCUU, (SEQ ID NO: 46)

CCUGACUGCGUGCAUGAAA, (SEQ ID NO: 47)

or

GCCUGGACAGCACUGAUUU, (SEQ ID NO: 48)

or its corresponding DNA version, i.e.,

TTCAGAATCGCCGCATGAAACACAAACGG, (SEQ ID NO: 12)

TCTACTCAACGTCTTCTGGCCTTGCCAAT, (SEQ ID NO: 13)

-continued

```
                                      (SEQ ID NO: 14)
CAAATCTGCCTGCGCCGGAGAGGACCATG, (SEQ ID NO: 15)
GGTTGAGTAAGGAGCCAAATACCTTGCGG, (SEQ ID NO: 16)
CGGGTTGAGTAAGGAGCCAAATA, (SEQ ID NO: 17)
CCGCATGAAACACAAACGGCAAA, (SEQ ID NO: 18)
CCCCAGCTTTCTACTCAACGTCT, (SEQ ID NO: 49)
GGGTTGAGTAAGGAGCCAA, (SEQ ID NO: 50)
GGTTGAGTAAGGAGCCAAA, (SEQ ID NO: 51)
GCTCTCAGAGGTCCAGATA, (SEQ ID NO: 52)
GGTTTCAGAATCGCCGCAT, (SEQ ID NO: 53)
TCAGAATCGCCGCATGAAA, (SEQ ID NO: 54)
TCGCCGCATGAAACACAAA, (SEQ ID NO: 55)
GCCGCATGAAACACAAACG, (SEQ ID NO: 56)
GCATGAAACACAAACGGCA, (SEQ ID NO: 57)
GCTTTCTACTCAACGTCTT, (SEQ ID NO: 58)
TCTCTGCCAAGTGGCACAA, (SEQ ID NO: 59)
GGACTCAGTTGTTCTGTTT, (SEQ ID NO: 60)
CCCGGCCCTGAGAATATAT, (SEQ ID NO: 61)
CCGGCCCTGAGAATATATT, (SEQ ID NO: 62)
GGTCAGTGAACAGAGTCAA, (SEQ ID NO: 63)
GCAGAAGTGGGCTTGTCAT, (SEQ ID NO: 64)
GCAGGTGTGTTTATAGCGT, (SEQ ID NO: 45)
GGAAAGCAGGAGGGAACAA, (SEQ ID NO: 65)
GCGTTGATGGACCGTTCTT, (SEQ ID NO: 66)
CCTGACTGCGTGCATGAAA,
or (SEQ ID NO: 67)
GCCTGGACAGCACTGATTT.
```

The iRNA agent can further contain a second strand having a second nucleotide sequence complementary to the first sequence.

Another aspect of this invention features a method of diagnosing primary or secondary bone marrow failure syndrome (BMFS) in a subject. The method includes two steps: (1) obtaining from the subject a biological sample containing HSCs, and (2) determining an expression level of a gene encoding VentX in the HSCs. The subject is determined to have BMFS if the expression level is higher than that in a control that does not have BMFS. Primary or secondary BMFS can be anemia, myelodysplasia syndrome, bone marrow injuries caused biologically (e.g., by a virus), physically (e.g. by radiation), chemically (e.g., by a toxin and chemotherapy agent), or environmentally (e.g., by pollution).

In still another aspect, the invention features a method of treating primary or secondary bone marrow failure syndrome. The method includes three steps: (1) isolating HSCs from a subject having primary or secondary bone marrow failure syndrome, (2) contacting the HSCs with an agent that inhibits expression or activity of a VentX polypeptide, thereby increasing expansion of the HSCs, and (3) administering to the subject an effective amount of the HSCs having undergone expansion. The isolating step can be performed by obtaining a biological sample containing HSCs from the subject and collecting HSCs from the biological sample. Primary or secondary bone marrow failure syndrome can be anemia, myelodysplasia syndrome, or a complication of chemotherapy or radiotherapy.

The details of one or more examples of the invention are set forth in the description below. Other features or advantages of the present invention will be apparent from the following detailed description of several embodiments, and also from the appended claims.

DETAILED DESCRIPTION OF THE INVENTION

VentX, a human homeobox transcriptional factor, is a novel antagonist of the canonical Wnt signaling. VentX has the amino acid and nucleotide sequences of SEQ ID NO: 1 and 4 (shown below), respectively.

The Amino Acid Sequence of VentX (SEQ ID NO: 1):

```
(Underlined: aa. 91-151/homeodomain, SEQ ID NO: 3)
mrlssspprg pqqlssfgsv dwlsqsscsg pthtprpadf slgslpgpgq tsgareppqa vsikeaagss nlpapertma glskepntlr aprvrtaftm eqvrtleqvf qhhqylsple rkrlaremql sevqiktwfq nrrmkhkrqm qdpqlhspfs gslhappafy stssglangl qllcpwapls gpqalmlppg sfwglcqvaq ealasagasc cgqplashpp tpgrpslgpa lstgprglca mpqtgdaf
``` the Nucleotide Sequence of VentX (SEQ ID NO: 4):

```
(underlined: coding sequence nt12 to 788,
SEQ ID NO: 2)
acctggccgc c atgcgcctc tcctcctccc cacctcgtgg ccgcagcag ctctccagct ttggctccgt ggactggctc tcccagagca gctgctcagg gccgacccac acccccaggc ctgccgactt ctccctgggg agcctccctg gcccaggcca gacatccggc gcccgggagc cccctcaggc cgtcagcatc aaggaggccg ccgggtcctc aaatctgcct gcgccggaga
```

-continued

```
ggaccatggc cggggttgagt aaggagccaa ataccttgcg ggcccccgt gtccgcacag ccttcaccat ggagcaggtc cgcaccttgg agggcgtctt ccagcaccac cagtacctga gccctctga gcggaagagg ctggccaggg agatgcagct ctcagaggtc cagataaaaa cctggtttca gaatcgccgc atgaaacaca aacggcaaat gcaggacccc cagctgcaca gccccttctc ggggtctctc catgcgcccc cagctttcta ctcaacgtct tctggccttg ccaatggcct gcagctgctg tgcccttggg caccccgtc cgggcccag gctctgatgc tgccccctgg ctccttctgg ggtctctgcc aagtggcaca agaggccctg gcatctgcgg gagcttcctg ctgcgggcag cctctggcgt cccaccccc taccccaggc cggccttcgc tgggaccagc cctgtccacg gggcccggg gcctgtgtgc tatgccacag acggggatg catttttgagg aggcacctct gactcccaca ctcgcggtct tgctgatcgc acctggctcc tacctggagg actcagttgt tctgtttaca tcctggtggc acctctcacc ctgacccaca caaaggttct ggagattact ggagaatata tataaatata tatatgtacg tatatatgta aatacacata tacgtatata taaatatata tatacatatg tgtgtgtata tatatatata tttttttttt tttttttttt tttgagacgg agtgttgctc tgtcacccag gctggagtgc aatgacgcaa tctcggctca ctgcaacctc cgcctcctgg gttcaagcga ttctccagcc tcagcctccc gagtagctgg gattacagac acccgccacc acgcccggct aattttttct attttttagta gaaatggggt ttcaccatgt tagccaggct ggtctcaaac tcctgaccct gtgatccgcc cgcctcggcc tcccaaagtg ctgggattac aggcatgagc cactgcaccc ggccctgaga atatatttat taaagccacc tcttcactga aagttaccga aagagtcggt ttaggaagga aacgaagggt cagtgaacag agtcaaatgc agaagtgggc ttgtcatggg tagggctttc ggcgtacgat aaaaggatca tttgttttt aaaaggggtt ggaaaaactg gttttccagt tggaaacagt aaaggttgta agctttgtgt gtacaaaaga aaacagggaa tgcaggtgtg tttatagcgt tgtggttcaa gtccctctta acaagaactc caaagctgga aagcaggagg gaacaaaggt gaacatgaag gcgaggatgc tggggccctg cagtgcgctc taggctgtgc gtgagccggg actgtaccca cagcttgctg agggctgctc ttcttgggcc agggaaagca gggcagccgg gacctgcggc tgtgcctgga ctgaagctgt cccgcaggtc cccaccctcc aacacgtgct cacctgtccc cctcctcgca gcagcctcgg gacaaaacaa tgactcaagg acagcacttc tcgcagaagg tctggaagtg cccagaatgg gaggcacgga agcccctccc ggggaggact cccgcgttga tggaccgttc ttggtgcaga ctcctgactg cgtgcatgaa acctgagaca agtgcaattc cttccatgtc gccccagagt gcccaggagg caggcagtgc ggggtgccca ggcagacggg ttcagcctgc agaactggag gcgacctgtg aaacccaccc gggcacccca acaggaacag aagcgtggtc ctgcggctgc gtccccagcg agtttcactt tccccttgct cgtttctccc ttgttgtaag tgtttacaac tggcatgtgc ttttaaacgt caggtaagag gggaacagct gctgtacatc gtcctggcga gtgacaatgt gacagaagcc tgggcgaggc cctcggaggg cagcagctgg acaggggcta ctgggtttgg cctggacagc actgatttgt ggatgtggat gggggcacgt tgtccgtgat aaaagtacaa gtgccctca caaaaaaaaa aaaaaaaa
```

VentX is a human homologue of the vertebrate *Xenopus* homeobox protein Xom of the BMP4 signaling pathway. It is a novel LEF/TCF-associated Wnt repressor and a putative tumor suppressor. Moreover, it controls expression of critical genes involved in cell proliferation and differentiation, such as p53/p16 and c-myc.

VentX is expressed under regulation in all lineages of hematopietic cells and its expression unexpectedly correlates in a reverse manner with the clonogenicity and expansion of HSCs. Thus, within the scope of this invention is a method of increasing expansion of HSCs that includes a step of transiently inhibiting VentX in human HSCs ex vivo.

Inhibitors of VentX include an iRNA agent, an antisense RNA (asRNA), a ribozyme, and an antibody.

An iRNA agent, e.g., a double stranded short-interfering RNA (siRNA), a short hairpin RNA (shRNA), or a single-stranded micro-RNA (miRNA), causes catalytic degradation of specific mRNAs. It can be used to lower or inhibit gene expression. It has sufficient sequence complementarity to a target RNA so as to induce degradation of the target RNA via RNA interference (RNAi), a sequence-specific or selective process by which a target molecule (e.g., a target gene, protein or RNA) is down-regulated. An iRNA agent can also be a DNA transcribable into an RNA.

Other such molecules that function via the mechanisms associated with RNAi can also be used including chemically modified siRNAs and vector driven expression of hairpin RNA that are then cleaved to siRNA.

The nucleic acid molecules or constructs that are useful as described herein include dsRNA (e.g., siRNA) molecules comprising 16-30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA of VentX, having a complement DNA sequence of SEQ ID NO:4, and the other strand is complementary to the first strand. The dsRNA molecules can be chemically synthesized, can transcribed be in vitro from a DNA template, or can be transcribed in vivo from, e.g., shRNA.

Antisense nucleic acids are useful for inhibiting VentX. Such antisense nucleic acid molecules are nucleic acid molecules whose nucleotide sequence is complementary to all or part of an mRNA encoding a VentX. An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences that flank the coding region and are not translated into amino acids.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double-stranded, i.e., dsRNA and dsDNA, respectively).

The polynucleotide can be administered by direct injection of a "naked" nucleic acid molecule (U.S. Pat. No. 5,679,647) or a nucleic acid molecule formulated in a composition with one or more other agents which facilitate uptake of the nucleic acid molecule by the cell, such as saponins (see, for example, U.S. Pat. No. 5,739,118) or cationic polyamines (see, for example, U.S. Pat. No. 5,837,533); by microparticle bombardment (for example, through use of a "gene gun"; Biolistic, Dupont); by coating the nucleic acid molecule with lipids, cell-surface receptors or transfecting agents; by encapsulation of the nucleic acid molecule in liposomes, microparticles, or microcapsules; by administration of the nucleic acid molecule linked to a peptide which is known to enter the nucleus; or by administration of the nucleic acid molecule linked to a ligand subject to receptor-mediated endocytosis, which can be used to target cell types specifically expressing the receptors. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479).

A nucleic acid-ligand complex can be formed in which the ligand comprises a fusogenic viral peptide to disrupt endosomes, allowing the nucleic acid to avoid lysosomal degradation; or the nucleic acid molecule can be targeted for cell specific uptake and expression in vivo by targeting a specific receptor. In addition, an efficient method for the introduction, expression and accumulation of antisense oligonucleotides in the cell nucleus is described in U.S. Pat. No. 6,265,167, which allows the antisense oligonucleotide to hybridise to the sense mRNA in the nucleus, and thereby prevents the antisense oligonucleotide being either processed or transported into the cytoplasm. The present invention also contemplates the intracellular introduction of the nucleic acid molecule and subsequent incorporation within host cell DNA for expression by homologous recombination known in the art.

The polynucleotide can also be incorporated into a suitable expression vector. A number of vectors suitable for gene therapy applications are known in the art (see, for example, Viral Vectors: Basic Science and Gene Therapy, Eaton Publishing Co. (2000)).

The expression vector may be a plasmid vector. Methods of generating and purifying plasmid DNA are rapid and straightforward. In addition, plasmid DNA typically does not integrate into the genome of the host cell, but is maintained in an episomal location as a discrete entity eliminating genotoxicity issues that chromosomal integration may raise. A variety of plasmids are now readily available commercially and include those derived from *Escherichia coli* and *Bacillus subtilis*, with many being designed particularly for use in mammalian systems. Examples of plasmids that may be used in the present invention include, but are not limited to, the eukaryotic expression vectors pRc/CMV (Invitrogen), pCR2.1 (Invitrogen), pAd/CMV and pAd/TR5/GFPq (Massie et al., 1998 Cytotechnology 28:53-64). In an exemplary embodiment, the plasmid is pRc/CMV, pRc/CMV2 (Invitrogen), pAdCMV5 (IRB-NRC), pcDNA3 (Invitrogen), pAdMLP5 (IRB-NRC), or PVAX Invitrogen).

The expression vector can be a viral-based vector. Examples of viral-based vectors include, but are not limited to, those derived from replication deficient retrovirus, lentivirus, adenovirus and adeno-associated virus. Retrovirus vectors and adeno-associated virus vectors are currently the recombinant gene delivery system of choice for the transfer of exogenous oligonucleotides or genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. Retroviruses, from which retroviral vectors may be derived include, but are not limited to, Moloney Murine Leukemia Virus, spleen necrosis virus, Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumour virus. Specific retroviruses include pLJ, pZIP, pWE and pEM, which are well known to those skilled in the art.

siRNA, miRNA, and asRNA molecules can be designed by methods well known in the art. These RNA molecules with homology sufficient to provide sequence specificity required to uniquely degrade any RNA can be designed using programs known in the art, including those maintained on websites for Ambion, Inc. and Dharmacon, Inc (see, siDESIGN CENTER) and "The siRNA User Guide," available on the Internet at mpibpc.gwdg.de/abteilungen/100/105/sirna.html. Systematic testing of several designed species for optimization of the siRNA, miRNA, and asRNA sequence can be routinely performed by those skilled in the art. Considerations when designing short interfering nucleic acid molecules include biophysical, thermodynamic, and structural considerations, base preferences at specific positions in the sense strand, and homology.

Ribozymes that have specificity for a VentX nucleic acid sequence can also be used to inhibit VentX expression. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff et al., 1988, Nature, 334:585-591) can be used to catalytically cleave mRNA transcripts to thereby inhibit translation of the protein encoded by the mRNA. Methods of designing and producing ribozymes are known in the art (see, e.g., Scanlon, 1999, Therapeutic Applications of Ribozymes, Humana Press). A ribozyme having specificity for a VentX nucleic acid molecule or fragment thereof can be designed based upon the nucleotide sequence of a VentX cDNA.

Antibodies (polyclonal and monoclonal antibodies) can be prepared by immunizing a suitable subject with a VentX polypeptide as an immunogen. Additionally, recombinant antibodies, such as chimeric and humanized monoclonal antibodies, including both human and non-human portions, which can be made using standard recombinant DNA techniques, are provided herein. Such chimeric and humanized monoclonal antibodies can be produced by recombinant DNA techniques known in the art, for example using methods described in WO 87/02671; European Patent Application 184,187; European Patent Application 171,496; European Patent Application 173,494; WO 86/01533; U.S. Pat. No. 4,816,567; European Patent Application 125,023; Better et al., Science, 240:1041-1043, 1988; Liu et al., Proc. Natl. Acad. Sci. USA 84:3439-3443, 1987; Liu et al., J. Immunol., 139:3521-3526, 1987; Sun et al., Proc. Natl. Acad. Sci. USA, 84:214-218, 1987; Nishimura et al., Canc. Res., 47:999-1005, 1987; Wood et al., Nature, 314:446-449, 1985; and Shaw et al., J. Natl. Cancer Inst., 80:1553-1559, 1988); Morrison, Science, 229:1202-1207, 1985; Oi et al., Bio/Techniques, 4:214, 1986; U.S. Pat. No. 5,225,539; Jones et al., Nature, 321:552-525, 1986; Verhoeyan et al., Science, 239: 1534, 1988; and Beidler et al., J. Immunol., 141:4053-4060, 1988.

Also within the scope of this invention are a method of diagnosing primary or secondary BMFS in a subject and a method of assessing prognosis of primary or secondary BMFS in a subject under a treatment therefor. Both methods include two steps: (1) obtaining a biological sample from the subject and (2) determining an expression level of a gene encoding VentX in the biological sample. The subject is determined to have BMFS if the expression level is higher than that in a control that does not have BMFS. The subject is determined to have a good prognosis if the expression level reduces after the treatment or have a poor prognosis if the expression level fails to reduce after the treatment.

The level of a VentX polypeptide or nucleic acid in a test sample can be evaluated by obtaining a test sample from a test subject and contacting the test sample with a compound or an agent capable of detecting a VentX polypeptide or nucleic acid (e.g., mRNA or genomic DNA probe). The "test sample" includes tissues, cells and biological fluids isolated from a subject, as well as tissues, cells and fluids present within a subject. The level of expression of the VentX gene can be measured in a number of ways, including measuring the mRNA encoded by the VentX gene; measuring the amount of polypeptide encoded by the VentX gene; or measuring the activity of polypeptide encoded by the VentX gene.

The level of mRNA corresponding to the VentX gene in a cell can be determined both by in situ and by in vitro formats. mRNA isolated from a test sample can be used in hybridization or amplification assays that include, Southern or Northern analyses, PCR analyses, and probe arrays. One preferred diagnostic method for the detection of mRNA levels involves contacting the isolated mRNA with a nucleic acid probe that can hybridize to the mRNA encoded by the VentX gene. The probe can be a full-length VentX nucleic acid, such as the nucleic acid of SEQ ID NO: 4 or a portion thereof, such as an oligonucleotide of at least 10 nucleotides in length and sufficient to specifically hybridize under stringent conditions to VentX mRNA or genomic DNA.

In one format, mRNA (or cDNA prepared from it) is immobilized on a surface and contacted with the probes, for example, by running the isolated mRNA on an agarose gel and transferring the mRNA from the gel to a membrane, such as nitrocellulose. In another format, the probes are immobilized on a surface and the mRNA (or cDNA) is contacted with the probes, for example, in a gene chip array. A skilled artisan can adapt known mRNA detection methods for use in detecting the level of mRNA encoded by the VentX gene.

The level of mRNA (or cDNA prepared from it) in a sample encoded by VentX gene can be evaluated with nucleic acid amplification, e.g., by standard PCR (U.S. Pat. No. 4,683, 202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115: 379-402, 1999), or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule comprising the nucleotide sequence flanked by the primers.

For in situ methods, a cell or tissue sample can be prepared and immobilized on a support, such as a glass slide, and then contacted with a probe that can hybridize to genomic DNA on chromosomes or mRNA that encodes the VentX polypeptide.

In another embodiment, the methods of the invention further include contacting a control sample with a compound or agent capable of detecting VentX mRNA, or genomic DNA, and comparing the presence of VentX mRNA or genomic DNA in the control sample with the presence of VentX mRNA or genomic DNA in the test sample.

The above-described nucleic acid-based diagnostic methods can provide qualitative and quantitative information to determine whether a subject has or is predisposed to a disease associated with aberrant VentX gene expression, e.g., BMFS.

A variety of methods can be used to determine the level of a VentX polypeptide. In general, these methods include contacting an agent that selectively binds to the polypeptide, such as an antibody, to evaluate the level of polypeptide in a sample. Antibodies can be polyclonal, or more preferably, monoclonal. An intact antibody, or a fragment thereof (e.g., Fab or $F(ab')_2$) can also be used. In a preferred embodiment, the antibody bears a detectable label. The term "labeled", with regard to the probe or antibody, is intended to encompass direct labeling of the probe or antibody by physically linking a detectable substance to the probe or antibody, as well as indirect labeling of the probe or antibody by reactivity with a detectable substance. For example, an antibody with a rabbit Fc region can be indirectly labeled using a second antibody directed against the rabbit Fc region, wherein the second antibody is coupled to a detectable substance. Examples of detectable substances are provided herein. Appropriate detectable substance or labels include radio isotopes (e.g., $^{125}I$, $^{131}I$, $^{35}S$, $^{3}H$, or $^{32}P$), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.).

The detection methods can be used to detect a VentX polypeptide in a biological sample in vitro as well as in vivo. In vitro techniques for detection of a VentX polypeptide include ELISAs, immunoprecipitations, immunofluorescence, EIA, RIA, and Western blotting analysis. In vivo techniques for detection of a VentX polypeptide include introducing into a subject a labeled anti-VentX antibody. For example, the antibody can be labeled with a detectable substance as described above. The presence and location of the detectable substance in a subject can be detected by standard imaging techniques.

The diagnostic methods described herein can identify subjects having, or at risk of developing, a disease or disorder associated with aberrant VentX expression or activity.

The prognostic assays described herein can be used to determine whether a subject is suitable to be administered with an agent (e.g., an agonist, antagonist, peptidomimetic, protein, peptide, nucleic acid, small molecule, or other drug candidate) to treat BMFS.

Also featured is a method of monitoring a treatment for BMFS in a subject. For this purpose, gene expression levels of VentX can be determined for test samples from a subject before, during, or after undergoing a treatment. An increase of the expression level of VentX after the treatment indicates that the subject can be further treated by the same treatment.

Information obtained from practice of the above diagnostic assays is useful in prognostication, identifying progression of, and clinical management of diseases and other deleterious conditions affecting an individual's health status. In preferred embodiments, the foregoing diagnostic assays provide information useful in prognostication, identifying progression of and management of BMFS that are characterized by a high level of VentX expression.

A "subject" refers to a human and a non-human animal. Examples of a non-human, from which the above-mentioned HSCs can be obtained, include, but are not limited to primate, dog, rodent, guinea pig, cat, horse, cow, sheep, and pig. Indeed, pet animals, farm animals, experimental animals, and disease-model animals are all contemplated. In a preferred embodiment, the subject is a human. In another embodiment, the subject is an experimental animal or disease-model animal.

The invention further features a method of treating conditions associated with an abnormally high level of a VentX polypeptide in HSCs with an effective amount of expanded HSCs as prepared in the manner as described above or with an effective amount of an agent that inhibits expression or activity of a VentX polypeptide. These conditions include primary or secondary BMSF, anemia (e.g., refractory anemia), myelodysplasia syndrome (e.g., hypocellular myelodysplasia syndrome), malignancies of the hematopoietic system (e.g., leukemia and lymphoma), and bone marrow injuries caused biologically (e.g., by viruses), physically (e.g. by radiation), chemically (e.g., by toxin and anti-cancer chemotherapy agents), or environmentally (e.g., by pollution).

"Treating" or "treatment" refers to administration of a composition containing an agent (which inhibits the expression or activity of VentX) or a composition containing HSCs pretreated with the agent to a subject, who has a condition (e.g., anemia and myelodysplasia syndrome), with the purpose to cure, alleviate, relieve, remedy, delay the onset of, or ameliorate the disorder, the symptom of the disorder, the disease state secondary to the disorder, or the predisposition toward the disorder.

An "effective amount" refers to an amount of the composition that is capable of producing a medically desirable result, e.g., as described above, in a treated subject. The treatment method can be performed in vivo or ex vivo, alone or in conjunction with other drugs or therapy. The actual effective amounts of drug can vary according to the specific drug or combination thereof being utilized, the particular composition formulated, the mode of administration, and the age, weight, condition of the patient, and severity of the symptoms or condition being treated. Dosages for a particular patient can be determined by one of ordinary skill in the art using conventional considerations, (e.g. by means of an appropriate, conventional pharmacological protocol).

One or more of the above-described compositions can be administered to an animal (e.g., a human) to modulate expression or activity of VentX or its homologus. A physician may, for example, prescribe a relatively low dose at first, subsequently increasing the dose until an appropriate response is obtained. In addition, it is understood that the specific dose level for any particular subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

The efficacy of treatment can be monitored either by measuring the amount of the target gene mRNA (e.g. using real time PCR) or the amount of polypeptide encoded by the target gene mRNA (Western blot analysis). As is well known in the art, the dosage for a patient depends upon various factors as described above. Dosages will vary, but a preferred dosage for administration of polynucleotide is about $10^6$ to $10^{12}$ copies of the polynucleotide molecule. This dose can be repeatedly administered as needed.

The polynucleotide can be prepared in any aqueous carrier, vehicle, or solution so as to provide a composition that is pharmaceutically suitable for in vivo administration. Methods of preparing aqueous solutions are well known to one of ordinary skill in the art. Preferably, the aqueous solutions is water, physiologically acceptable aqueous solutions containing salts and/or buffers, such as phosphate buffered saline (PBS), or any other aqueous solution/surfactant acceptable for administration to a animal or human. Such solutions are well known to a person skilled in the art and include, but are not limited to, distilled water, de-ionized water, pure or ultrapure water, saline, PBS, and solutions containing usual buffers which are compatible with nucleic acids. The composition may also contain sodium chloride and glucose or mannitol to make the solution isotonic. The composition may contain suitable auxiliary components, such as pH, osmolarity, and tonicity adjusting agents.

The polynucleotide can be delivered using polymeric, biodegradable microparticle, or microcapsule delivery devices known in the art. Another way to achieve uptake of the polynucleotides is using liposomes, prepared by standard methods. The polynucleotide can be incorporated alone into these delivery vehicles or co-incorporated with tissue-specific antibodies. Further, tissue specific targeting can be achieved by the use of tissue-specific transcriptional regulatory elements that are known in the art.

The polynucleotide can be administered parenterally. The term "parenteral" as used herein refers to injections, such as intravenous, intraarterial, intramedulllary, intraosseous, and intrathecal injections, as well as any suitable infusion techniques.

The expanded HSCs may be formulated for administration to a patient, for example, by dissociating the cells (e.g., by mechanical dissociation) and intimately admixing the cells with a pharmaceutically acceptable carrier (e.g., phosphate buffered saline solution). They can be administered to individuals through injection or infusion.

Both heterologous and autologous HSCs can be used. In the former case, HLA-matching should be conducted to avoid or minimize host reactions. In the latter case, autologous cells are enriched and purified from a subject and stored for later use. The cells may be cultured in the presence of host or graft T cells ex vivo and re-introduced into the host. This may have the advantage of the host recognizing the cells as self and better providing reduction in T cell activity.

The present invention provides for pharmaceutical compositions containing an agent (which inhibits the expression or activity of VentX) or a composition containing HSCs pretreated with the agent. Pharmaceutical compositions can be prepared by mixing a therapeutically effective amount of the active agents or HSCs and optionally other active agents with a pharmaceutically acceptable carrier. The carrier can have different forms, depending on the route of administration. Examples of other active agents include active compounds known to expand HSCs.

The above-described pharmaceutical compositions can be prepared by using conventional pharmaceutical excipients and methods of preparation. All excipients may be mixed with disintegrating agents, solvents, granulating agents, moisturizers, and binders.

The phrase "pharmaceutically acceptable" refers to molecular entities and other ingredients of such compositions that are physiologically tolerable and do not typically produce unwanted reactions when administered to a human. Preferably, the term "pharmaceutically acceptable" means approved by a regulatory agency of the federal or a state government or listed in the U.S. Pharmacopeia or other generally recognized pharmacopeia for use in mammals, and more particularly in humans. Pharmaceutically acceptable salts, esters, amides, and prodrugs refers to those salts (e.g., carboxylate salts, amino acid addition salts), esters, amides, and prodrugs which are, within the scope of sound medical judgment, suitable for use in contact with the tissues of patients without undue toxicity, irritation, allergic response, and the like, commensurate with a reasonable benefit/risk ratio, and effective for their intended use.

A carrier applied to the pharmaceutical compositions described above refers to a diluent, excipient, or vehicle with which a compound is administered. Such pharmaceutical carriers can be sterile liquids, such as water and oils. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th edition.

The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the above-described composition. Dosages and administration regimen can be adjusted depending on the age, sex, physical condition of administered as well as the benefit of the conjugate and side effects in the patient or mammalian subject to be treated and the judgment of the physician, as is appreciated by those skilled in the art.

Finally, the invention features a method of delivering a gene to treat immune or metabolic diseases by gene therapy. The HSCs described herein can be used to express exogenous, recombinant polypeptide. Thus, within the scope of this invention are such HSCs, which contain a recombinant nucleic acid. The recombinant nucleic acid can encode a polypeptide and HSCs can contain an mRNA encoding the polypeptide.

Accordingly, the invention features a method for introducing a heterologous nucleic acid in a subject. The method includes the steps of expanding and transfecting HSCs, where at least one of the HSCs includes a heterologous nucleic acid, and administering the cell into a subject in need thereof. The heterologous nucleic acid encodes a polypeptide of interest.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell. Similarly, a heterologous protein indicates that the protein comprises two or more subsequences that are not found in the same relationship to each other in nature (e.g., a "fusion protein," where the two subsequences are encoded by a single nucleic acid sequence). Such protein can be generated by recombinant techniques.

The term "recombinant" when used with reference, e.g., to a cell, nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

The above-described HSCs and methods can be used in various gene therapy methods known in the art. Gene therapy includes both ex vivo and in vivo techniques. Specifically, the above-described HSCs can be genetically engineered ex vivo with an oligonucleotide modulator or a nucleic acid molecule encoding the modulator, with the engineered cells then being provided to a patient to be treated. Cell cultures may be formulated for administration to a patient, for example, by dissociating the cells (e.g., by mechanical dissociation) and intimately admixing the cell with a pharmaceutically acceptable carrier (e.g., phosphate buffered saline solution). The engineered cells are typically autologous so as to circumvent xenogeneic or allotypic rejection. Such ex vivo methods are well known in the art.

The cells can be engineered by administration of the polynucleotide using techniques as described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All publications cited herein hereto are incorporated by reference.

Example 1

VentX Expression is Regulated During Hematopoiesis and Erythropoiesis

Bone marrow (BW) samples were obtained from discarded femoral head tissue after hip replacement surgery from Brigham and Women's Hospital, with institutional IRB approval. After Ficoll separation of mononuclear cells, CD34+ cells were enriched using magnetically activated cell sorting CD34$^+$ progenitor kit (Miltenyi Biotec). The purity of the BW CD34+ cells was over 95%, as assessed by flow cytometry as described in Rizo et al., 2008.

Total RNA was isolated by the TRIzol method, and same amount of RNA was used for first-strand cDNA synthesis with SuperSript First-Strand Synthesis System (Invitrogen)

according to the manufacturer's protocol. To determine VentX mRNA level, the cDNA was then used for real-time PCR of VentX with primers: 5'-CCGTCAGCATCAAG-GAGG-3' (SEQ ID NO: 19) and 5'-CTGGACCTCT-GAGAGCTGC-3' (SEQ ID NO: 20). Real-time PCR was also performed with SYBR Green on a LightCycler® 480 system (480 Real-Time PCR System; Roche).

The results show that VentX expression was elevated during maturation of erythrocytes. More specifically, VentX expression was negligible in the CD34+CD38− cells, significantly up-regulated in the CD34+CD38+ cells, and further elevated in progenitor cells of myeloid lineage, e.g., megakaryocyte-erythroid progenitors (MEPs), granulocyte-macrophage progenitors (GMs), and common myeloid progenitors (CMPs). Elevated expression pattern of VentX during erythropoiesis was the same as those during other hematopoietic processes, such as during lymphopoiesis. There was no significant difference of VentX expression between the above-mentioned three different subgroups of myeloid lineage, i.e., MEP, GM, and CMP.

Example 2

VentX Regulates Expansion of Human HSCs Ex-Vivo

Human BW CD34+ cells were obtained as described in Example 1. VentX expression in these cells was knocked down with a lentiviral-based shRNA approach.

Briefly, the lentiviral vector pHAGE-CMV-eGFPW that expresses a shRNA targeting VentX (pHAGE-shVentX) was used for the transduction of bone marrow CD34+ cells. This lentiviral vector contains an internal ribosome entry site (IRES) that allows simultaneous expression of GFP to monitor transduction rate or for cell sorting. The corresponding DNA sequence of VentX shRNA is SEQ ID NO: 12 or 14.

A non-effective sequence targeting GFP (pHAGE-shGFP) was used as a control. Lentiviral packaging was carried out in Dana-Farber/Harvard Cancer Center Vector Core Facility and viral supernatants were stored at −70° C. in aliquots until use. CD34+ cells were first cultured in IMDM medium containing 10% FBS, stem cell factor (SCF, 100 ng/mL), Flt3 ligand (100 ng/mL), thrombopoietin (TPO, 100 ng/mL), interleukin-3 (IL-3, 10 ng/mL), and IL-6 (10 ng/mL) (PeproTech) for 2 days and then transduced with a Multiplicity of Infection (MOI) of 5 in the presence of 4 µg/ml polybrene. GFP positive cells were sorted by FACSAria high-speed sorter (BD Bioscience) at 24 h after transduction (Dana-Farber Cancer Institute Flow Cytometry Core Facility).

Assays for in vitro colony-forming cells (CFCs) were performed by plating sorted GFP positive CD34+ cells ($1 \times 10^4$ per dish) in triplicates in complete methylcellulose medium (Methocult G F, H4434; Stem Cell Technologies), which contains a mixture of recombinant human cytokines (SCF, IL-3, GM-CSF, and erythropoietin). Colonies were counted after 14 days of incubation at 37° C. and classified according to standard criteria.

For long-term culture-initiating cell (LTC-IC) assay, transduced GFP positive cells were sorted on M2-10B4 murine fibroblast cells in limiting dilutions from 30 to 900 cells per well in 96-well plates. Cultures were weekly fed with a new medium. After 5 weeks of culture, all cells from the wells were transferred to 35 mm petri dish in complete methylcellulose medium mentioned above. After an additional 2 weeks of culture, wells were scored as positive or negative to yield the LTC-IC frequency.

The results show that the transduction rates of pHAGE-shVentX and pHAGE-shGFP were about 20%. Using quantitative PCR approach, the efficiency of VentX knockdown in pHAGE-shVentX-transduced CD34+ cells was determined to be about 30%. The positively transduced cells were plated in cytokine supplemented stroma-free liquid cultures and the cell numbers were counted weekly up to 4 weeks. Plotting of weekly cell counts of demi-depopulated cultures shows that knockdown of VentX expression in CD34+ cells led to a ~5-fold increase in total cell number in comparison with the control cells from three independent experiments after the cells were cultured for 4 weeks.

As determined by the colony-forming cell (CFC) assay, knockdown of VentX resulted in a ~2-fold increase in the formation of BFU-E/CFU-E, CFU-GM and CFU-G/CFU-M colonies. The total number of progeny cells increased about ~3 fold based on the CFC assay. This knockdown promoted the expansion of all lineages of hematopoietic cell, especially erythroid lineage colony formation. Consistently, LTC-IC frequency increased ~3 fold in shVentX transduced CD34+ cells. In addition, this knockdown led to a 30% increase on the percentage of the CD34+ cells in the ex vivo liquid culture.

A time-course FACS analysis revealed that knockdown of VentX helped preserve the CD34+ cells population up to 4 weeks. It also increased the population of most primitive CD34+CD38− cells. In sum, VentX knockdown helped maintain the CD34+ cell pools and promote CD34+ cell expansion.

Example 3

Transient Knockdown of VentX by a Short Interfering RNA (siRNA) Promotes HSC Expansion Human BW CD34+ cells were obtained as described in Example 1. VentX expression in these cells was knocked down using a siRNA approach. More specifically, short oligonucleotides targeting VentX, siVentX were transfected into the above-mentioned BW CD34+ cells through electroporation using the Human CD34+ cell Nucleofector Kit (Lonza) according to the manufacturer's instructions.

Briefly, $1 \times 10^6$ CD34+ cells were dispersed into a 100 µl nucleofector solution with 0.5 nmol of either VentX siRNA (SEQ ID NO: 5) or non-effective GFP siRNA. Electroporation of these cells was performed using nucleofector II Device (Lonza). The electerophorated cells were incubated overnight with 1 ml pre-warmed IMDM medium containing 10% FBS and the above-mentioned cytokines.

The results, based on quantitative RT-PCR, show a ~70% of knockdown of VentX in the CD34+ cells by siRNA transfection. Consistent with those of the above-mentioned lentiviral-mediated approach, transient knockdown of VentX in CD34+ cells also led to ~2-fold expansion of HSCs in comparison with siGFP-transfected cells during 2 weeks culture. Likewise, siVentX-transfected cells showed an increase on the percentage of CD34+ cells. The CFC assay also shows that transient knockdown of VentX resulted in a ~2-fold increase in formation of BFU-E/CFU-E colonies and CFU-GM colonies and in total number of progeny cells. In sum, this siRNA approach was as effective as the above-mentioned lentiviral-based shRNA approach.

Example 4

Overexpression of VentX Blocks the CD34+ Cells Expansion

Human BW CD34+ cells were obtained as described in Example 1. These cells were transfected with pCS2-GFP or pCS2-GFPVentX plasmid using the Human CD34+ cell Nucleofector Kit (Lonza) as described above. GFP-positive cells were sorted by FACSAria high-speed sorter after transfected for 24 hours.

The results show that the colony formation of CD34+ cells was largely abrogated by the enforced expression of VentX. Furthermore, StemRegenin 1 (SR1)-mediated expansion of human CD34+ cells is blocked by overexpression of VentX.

Note that StemRegenin 1 (SR1) is an Aryl hydrocarbon receptor antagonist. The results also show that SR1 inhibited expression of VentX in the CD34+ cells and increased expansion of these CD34+ cells. Thus, downregulation of VentX is required for expansion of the CD34+ cells.

Example 5

VentX Regulates HSC Expansion In Vivo

To determine whether VentX promotes HSC expansion in vivo, eight weeks old NOD.Cg-Prkdc$^{scid}$ Il2rg$^{tm1Wjl}$/SzJ mice (commonly known as NOD scid gamma; NSG) were purchased from the Jackson Laboratory and maintained in specific pathogen-free conditions. Before transplantations, mice were sublethally irradiated with 100 Rads. About $1 \times 10^6$ CD34+ cells were transduced with VentX or GFP shRNA lentivirus. At 24 h after transduction, all cells ($1 \times 10^6$, with ~20% GFP positive cells) or positively transduced cells ($2 \times 10^4$, with all GFP positive) were injected into recipient mice. The human CD45+ cells were analyzed with FACS from the bone marrow of recipient mice. For secondary transplantation, the bone marrow of chimeric primary recipient mice was injected into secondary recipient NSG mice without further purification of human cells.

The results show that the human cells engraftment rate increased about 1.5~2-fold in shVentX transduced CD34+ cells in comparison with CD34+ cells transduced with shGFP. Notably, knockdown of VentX allowed the development of all lineages of hematopoietic cells. The development of myeloid lineage (CD14+ cells) appeared to be slightly impaired in comparison with other lineages.

Given that the lentiviral transduction rate of the CD34+ cells was only about 20%, to further explore the effects of VentX knockdown on the expansion of HSCs, the positively transduced CD34+ cells were purified and then transplanted into NSG mice. Thirteen weeks after the transplantation, the percentage of human CD45$^+$ cells was determined by FACS analysis. Strikingly, the percentage of human CD45$^+$ cells was increased by up to 20 folds in shVentX transduced CD34+ cells in comparison with CD34+ cells transduced with shGFP.

To examine the effects of VentX on long term engraftment of human CD34+ cells, secondary transplantation experiments were performed. While no mice with the control shGFP transduced CD34+ cells show detectable secondary engraftment, two mice with shVentX transduced CD34+ cells show positive human cells engraftment (0.25% and 0.28%, respectively).

Example 6

VentX Targets the Cell Cycle Regulators in CD34+ Cells

VentX is a regulator of the Wnt signaling pathway and several components of cell cycle machinery, such as Cyclin D1, p21 and p16$^{ink4a}$. The levels of p21, p16$^{ink4}$, C-myc, and Cyclin D1 were determined using quantitative PCR with the following primers:

```
p21:
                                        (SEQ ID NO: 21)
5'-AAACTTTGGAGTCCCCTCAC-3'
and (SEQ ID NO: 22)
5'-AAAGGCTCAACACTGAGACG-3';

p16:
                                        (SEQ ID NO: 23)
5'-CTTCCCCCACTACCGTAAAT-3'
and (SEQ ID NO: 24)
5'-TGCTCACTCCAGAAAACTCC-3';

C-myc:
                                        (SEQ ID NO: 25)
5'-CAGCTGCTTAGACGCTGGATT-3'
and (SEQ ID NO: 26)
5'-GTAGAAATACGGCTGCACCGA-3';
and Cyclin D1:
                                        (SEQ ID NO: 27)
5'-GTTCGTGGCCTCTAAGATG-3'
and (SEQ ID NO: 28)
5'-TTGTTCACCAGGAGCAGC-3'.
```

The results show that overexpression of VentX increased the expression of p21 and p16$^{ink4a}$, but downregulated the expression of Cyclin D1 and C-myc in CD34+ cells. The results were further confirmed by loss-of-function approach, in which knockdown of VentX decreased expression of p21, but increased the expression of Cyclin D1 and C-myc. Also based on FACS analysis, knockdown of VentX raised the level of the Cyclin D1 protein.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

---

What is claimed is:

1. A method of treating primary or secondary bone marrow failure syndrome, the method comprising:

obtaining hematopoietic stem cells from a subject that has primary or secondary bone marrow failure syndrome;

detecting a higher expression level of a gene encoding VentX in the hematopoietic stem cells as compared to that in control hematopoietic stem cells;

generating expanded hematopoietic stem cells by (a) contacting isolated hematopoietic stem cells with an IRNA agent having the sequence of SEQ ID NO: 5 that inhibits the expression or activation of a VentX polypeptide, and (b) incubating the isolated hematopoietic stem cells thus contacted under conditions allowing expansion of the isolated cells, whereby expanded hematopoietic stem cells are generated; and administering to the subject an effective amount of the expanded hematopoietic stem cells.

2. The method of claim 1, wherein the obtaining step is carried out by isolating the hematopoietic stem cells from a bone marrow or peripheral blood sample from the subject.

3. The method of claim 1, wherein the primary or secondary bone marrow failure syndrome is anemia, myelodysplasia syndrome, or a complication of chemotherapy or radiotherapy.

4. The method of claim 3, wherein the primary or secondary bone marrow failure syndrome is anemia.

5. The method of claim 3, wherein the primary or secondary bone marrow failure syndrome is myelodysplasia syndrome.

6. The method of claim 3, wherein the primary or secondary bone marrow failure syndrome is a complication of chemotherapy.

7. The method of claim 1, wherein step (a) is carried out by introducing into the cells an oligonucleotide consisting of the sequence of SEQ ID NO:5.

8. The method of claim 1, wherein step (a) is carried out by introducing into the cells an expression construct that expresses a short hairpin RNA (shRNA) having the sequence of SEQ ID NO:5.

9. The method of claim 1, wherein the detecting step is carried out by detecting a higher level of a VentX polypeptide.

10. The method of claim 1, wherein the detecting step is carried out by detecting a higher level of a VentX mRNA.

* * * * *

SEQUENCE LISTING

<160> NUMBER OF SEQ ID NOS: 67

<210> SEQ ID NO 1
<211> LENGTH: 258
<212> TYPE: PRT
<213> ORGANISM: Homo sapiens

<400> SEQUENCE: 1

Met Arg Leu Ser Ser Pro Pro Arg Gly Pro Gln Gln Leu Ser Ser
1               5                   10                  15

Phe Gly Ser Val Asp Trp Leu Ser Gln Ser Ser Cys Ser Gly Pro Thr
                20                  25                  30

His Thr Pro Arg Pro Ala Asp Phe Ser Leu Gly Ser Leu Pro Gly Pro
                35                  40                  45

Gly Gln Thr Ser Gly Ala Arg Glu Pro Pro Gln Ala Val Ser Ile Lys
            50                  55                  60

Glu Ala Ala Gly Ser Ser Asn Leu Pro Ala Pro Glu Arg Thr Met Ala
65                  70                  75                  80

Gly Leu Ser Lys Glu Pro Asn Thr Leu Arg Ala Pro Arg Val Arg Thr
                85                  90                  95

Ala Phe Thr Met Glu Gln Val Arg Thr Leu Glu Gly Val Phe Gln His
                100                 105                 110

His Gln Tyr Leu Ser Pro Leu Glu Arg Lys Arg Leu Ala Arg Glu Met
            115                 120                 125

Gln Leu Ser Glu Val Gln Ile Lys Thr Trp Phe Gln Asn Arg Arg Met
130                 135                 140

Lys His Lys Arg Gln Met Gln Asp Pro Gln Leu His Ser Pro Phe Ser
145                 150                 155                 160

Gly Ser Leu His Ala Pro Pro Ala Phe Tyr Ser Thr Ser Ser Gly Leu
                165                 170                 175

Ala Asn Gly Leu Gln Leu Leu Cys Pro Trp Ala Pro Leu Ser Gly Pro
            180                 185                 190

Gln Ala Leu Met Leu Pro Pro Gly Ser Phe Trp Gly Leu Cys Gln Val
        195                 200                 205

Ala Gln Glu Ala Leu Ala Ser Ala Gly Ala Ser Cys Cys Gly Gln Pro
    210                 215                 220

Leu Ala Ser His Pro Pro Thr Pro Gly Arg Pro Ser Leu Gly Pro Ala
225                 230                 235                 240

Leu Ser Thr Gly Pro Arg Gly Leu Cys Ala Met Pro Gln Thr Gly Asp
                245                 250                 255

Ala Phe

<210> SEQ ID NO 2
<211> LENGTH: 777
<212> TYPE: DNA
<213> ORGANISM: Artificial Sequence
<220> FEATURE:
<223> OTHER INFORMATION: Synthetic oligonucleotide

<400> SEQUENCE: 2
atgcgcctct cctcctcccc acctcgtggc ccgcagcagc tctccagctt tggctccgtg      60
gactggctct cccagagcag ctgctcaggg ccgacccaca cccccaggcc tgccgacttc     120
tccctgggga gctccctgg cccaggccag acatccggcg cccggagcc ccctcaggcc      180 gtcagcatca aggaggccgc cgggtcctca aatctgcctg cgccggagag gaccatggcc     240
gggttgagta aggagccaaa taccttgcgg gcccccgtg tccgcacagc cttcaccatg      300
gagcaggtcc gcaccttgga gggcgtcttc agcaccacc agtacctgag ccctctggag     360
cggaagaggc tggccaggga gatgcagctc tcagaggtcc agataaaaac ctggtttcag     420
aatcgccgca tgaaacacaa acggcaaatg caggaccccc agctgcacag ccccttctcg     480
gggtctctcc atgcgccccc agctttctac tcaacgtctt ctggccttgc caatggcctg     540

```
cagctgctgt gcccttgggc acccctgtcc gggccccagg ctctgatgct gcccctggc    600 tccttctggg gtctctgcca agtggcacaa gaggccctgg catctgcggg agcttcctgc    660
tgcgggcagc ctctggcgtc ccaccccct accccaggcc ggccttcgct gggaccagcc    720
ctgtccacgg ggccccgggg cctgtgtgct atgccacaga cgggggatgc attttga       777
```

<210> SEQ ID NO 3
<211> LENGTH: 61
<212> TYPE: PRT
<213> ORGANISM: Artificial Sequence
<220> FEATURE:
<223> OTHER INFORMATION: Synthetic peptide

<400> SEQUENCE: 3

Ala Pro Arg Val Arg Thr Ala Phe Thr Met Glu Gln Val Arg Thr Leu
1               5                   10                  15

Glu Gly Val Phe Gln His His Gln Tyr Leu Ser Pro Leu Glu Arg Lys
                20                  25                  30

Arg Leu Ala Arg Glu Met Gln Leu Ser Glu Val Gln Ile Lys Thr Trp
            35                  40                  45

Phe Gln Asn Arg Arg Met Lys His Lys Arg Gln Met Gln
        50                  55                  60

<210> SEQ ID NO 4
<211> LENGTH: 2428
<212> TYPE: DNA
<213> ORGANISM: Homo sapiens

<400> SEQUENCE: 4

```
acctggccgc catgcgcctc tcctcctccc cacctcgtgg cccgcagcag ctctccagct    60
ttggctccgt ggactggctc tcccagagca gctgctcagg gccgacccac accccccaggc   120 ctgccgactt ctccctgggg agcctccctg gcccaggcca gacatccggc gcccgggagc   180
cccctcaggc cgtcagcatc aaggaggccg ccgggtcctc aaatctgcct cgcgcggaga   240
ggaccatggc cgggttgagt aaggagccaa ataccttgcg ggccccccgt gtccgcacag   300
ccttcaccat ggagcaggtc cgcaccttgg agggcgtctt ccagcaccac cagtacctga   360
gccctctgga gcggaagagg ctggccaggg agatgcagct ctcagaggtc cagataaaaa    420
cctggtttca gaatcgccgc atgaaacaca acggcaaat gcaggacccc cagctgcaca    480 gcccccttctc ggggtctctc catgcgcccc cagcttttcta ctcaacgtct tctggccttg   540
ccaatggcct gcagctgctg tgcccttggg caccctgtc cgggcccag gctctgatgc     600 tgcccccctgg ctccttctgg gtctctgcc aagtggcaca gaggccctg gcatctgcgg     660 gagcttcctg ctgcgggcag cctctggcgt ccaccccc taccccaggc cggccttcgc     720
tgggaccagc cctgtccacg ggggccccggg gcctgtgtgc atgccacag acggggggatg     780 cattttgagg aggcacctct gactcccaca ctcgcggtct tgctgatcgc acctggctcc    840
tacctggagg actcagttgt tctgtttaca tcctggtggc acctctcacc ctgacccaca    900
caaaggttct ggagattact ggagaatata tataaatata tatgtacg tatatatgta     960 aatacacata tacgtatata taaatatata tatacatatg tgtgtgtata tatatatata   1020
tttttttttt tttttttttt tttgagacgg agtgttgctc tgtcacccag gctggagtgc   1080
aatgacgcaa tctcggctca ctgcaacctc cgcctcctgg gttcaagcga ttctccagcc   1140
tcagcctccc gagtagctgg gattacagac acccgccacc acgcccggct aattttttct   1200 attttttagta gaaatggggt ttcaccatgt tagccaggct ggtctcaaac tcctgaccct   1260
```

-continued

```
gtgatccgcc cgcctcggcc tcccaaagtg ctgggattac aggcatgagc cactgcaccc    1320
ggccctgaga atatatttat taaagccacc tcttcactga aagttaccga aagagtcggt    1380
ttaggaagga aacgaagggt cagtgaacag agtcaaatgc agaagtgggc ttgtcatggg    1440
tagggctttc ggcgtacgat aaaaggatca tttgtttttt aaaggggtt ggaaaaactg     1500 gttttccagt tggaaacagt aaaggttgta agctttgtgt gtacaaaaga aaacagggaa    1560
tgcaggtgtg tttatagcgt tgtggttcaa gtccctctta acaagaactc caaagctgga    1620
aagcaggagg gaacaaaggt gaacatgaag gcgaggatgc tggggccctg cagtgcgctc    1680
taggctgtgc gtgagccggg actgtaccca cagcttgctg agggctgctc ttcttgggcc    1740
agggaaagca gggcagccgg gacctgcggc tgtgcctgga ctgaagctgt cccgcaggtc    1800 cccacccctcc aacacgtgct cacctgtccc cctcctcgca gcagcctcgg gacaaaacaa   1860
tgactcaagg acagcacttc tcgcagaagg tctggaagtg cccagaatgg gaggcacgga    1920
agcccctccc ggggaggact cccgcgttga tggaccgttc ttggtgcaga ctcctgactg     1980
cgtgcatgaa acctgagaca gtgcaattc cttccatgtc gccccagagt gcccaggagg     2040
caggcagtgc ggggtgccca ggcagacggg ttcagcctgc agaactggag gcgacctgtg    2100
aaacccaccc gggcacccca acaggaacag aagcgtggtc ctgcggctgc gtccccagcg    2160
agtttcactt tccccttgct cgtttctccc ttgttgtaag tgtttacaac tggcatgtgc    2220
ttttaaacgt caggtaagag gggaacagct gctgtacatc gtcctggcga gtgacaatgt    2280
gacagaagcc tgggcgaggc cctcggaggg cagcagctgg acaggggcta ctgggtttgg    2340
cctggacagc actgatttgt ggatgtggat gggggcacgt tgtccgtgat aaaagtacaa    2400
gtgcccctca caaaaaaaaa aaaaaaaa                                        2428
```

<210> SEQ ID NO 5
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 5
uucagaaucg ccgcaugaaa cacaaacgg                                       29

<210> SEQ ID NO 6
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 6
ucuacucaac gucuucuggc cuugccaau                                       29

<210> SEQ ID NO 7
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 7
caaaucugcc ugcgccggag aggaccaug                                       29

```
<210> SEQ ID NO 8
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 8
gguugaguaa ggagccaaau accuugcgg                                              29

<210> SEQ ID NO 9
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 9
cggguugagu aaggagccaa aua                                                    23

<210> SEQ ID NO 10
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 10
ccgcaugaaa cacaaacggc aaa                                                    23

<210> SEQ ID NO 11
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 11
ccccagcuuu cuacucaacg ucu                                                    23

<210> SEQ ID NO 12
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 12
ttcagaatcg ccgcatgaaa cacaaacgg                                              29

<210> SEQ ID NO 13
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 13
tctactcaac gtcttctggc cttgccaat                                              29

<210> SEQ ID NO 14
<211> LENGTH: 29
<212> TYPE: DNA
<213> ORGANISM: Artificial Sequence
<220> FEATURE:
<223> OTHER INFORMATION: Synthetic oligonucleotide
```

-continued

<400> SEQUENCE: 14
caaatctgcc tgcgccggag aggaccatg                                29

<210> SEQ ID NO 15
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 15
ggttgagtaa ggagccaaat accttgcgg                                29

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
cgggttgagt aaggagccaa ata                                      23

<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 17
ccgcatgaaa cacaaacggc aaa                                      23

<210> SEQ ID NO 18
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 18
ccccagcttt ctactcaacg tct                                      23

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 19
ccgtcagcat caaggagg                                            18

<210> SEQ ID NO 20
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 20
ctggacctct gagagctgc                                           19

```
<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
aaactttgga gtcccctcac                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
aaaggctcaa cactgagacg                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
cttcccccac taccgtaaat                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
tgctcactcc agaaaactcc                                               20

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 25
cagctgctta gacgctggat t                                             21

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26
gtagaaatac ggctgcaccg a                                             21

<210> SEQ ID NO 27
<211> LENGTH: 19
<212> TYPE: DNA
<213> ORGANISM: Artificial Sequence
<220> FEATURE:
<223> OTHER INFORMATION: Synthetic oligonucleotide
```

<400> SEQUENCE: 27
gttcgtggcc tctaagatg                    19

<210> SEQ ID NO 28
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 28
ttgttcacca ggagcagc                     18

<210> SEQ ID NO 29
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 29
ggguugagua aggagccaa                    19

<210> SEQ ID NO 30
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 30
gguugaguaa ggagccaaa                    19

<210> SEQ ID NO 31
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 31
gcucucagag guccagaua                    19

<210> SEQ ID NO 32
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 32
gguuucagaa ucgccgcau                    19

<210> SEQ ID NO 33
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 33
ucagaaucgc cgcaugaaa                    19

```
<210> SEQ ID NO 34
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 34
ucgccgcaug aaacacaaa                                               19

<210> SEQ ID NO 35
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 35
gccgcaugaa acacaaacg                                               19

<210> SEQ ID NO 36
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 36
gcaugaaaca caaacggca                                               19

<210> SEQ ID NO 37
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 37
gcuuucuacu caacgucuu                                               19

<210> SEQ ID NO 38
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 38
ucucugccaa guggcacaa                                               19

<210> SEQ ID NO 39
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 39
ggacucaguu guucuguuu                                               19

<210> SEQ ID NO 40
<211> LENGTH: 19
<212> TYPE: RNA
<213> ORGANISM: Artificial Sequence
<220> FEATURE:
<223> OTHER INFORMATION: Synthetic oligonucleotide
```

```
<400> SEQUENCE: 40
cccggcccug agaauauau                                              19

<210> SEQ ID NO 41
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 41
ccggcccuga gaauauauu                                              19

<210> SEQ ID NO 42
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 42
ggucagugaa cagagucaa                                              19

<210> SEQ ID NO 43
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 43
gcagaagugg gcuugucau                                              19

<210> SEQ ID NO 44
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 44
gcaggugugu uuauagcgu                                              19

<210> SEQ ID NO 45
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 45
ggaaagcagg agggaacaa                                              19

<210> SEQ ID NO 46
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 46
gcguugaugg accguucuu                                              19
```

```
<210> SEQ ID NO 47
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 47
ccugacugcg ugcaugaaa                                              19

<210> SEQ ID NO 48
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 48
gccuggacag cacugauuu                                              19

<210> SEQ ID NO 49
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 49
gggttgagta aggagccaa                                              19

<210> SEQ ID NO 50
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 50
ggttgagtaa ggagccaaa                                              19

<210> SEQ ID NO 51
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 51
gctctcagag gtccagata                                              19

<210> SEQ ID NO 52
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 52
ggtttcagaa tcgccgcat                                              19

<210> SEQ ID NO 53
<211> LENGTH: 19
<212> TYPE: DNA
<213> ORGANISM: Artificial Sequence
<220> FEATURE:
<223> OTHER INFORMATION: Synthetic oligonucleotide
```

<400> SEQUENCE: 53
tcagaatcgc cgcatgaaa                                                 19

<210> SEQ ID NO 54
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 54
tcgccgcatg aaacacaaa                                                 19

<210> SEQ ID NO 55
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 55
gccgcatgaa acacaaacg                                                 19

<210> SEQ ID NO 56
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 56
gcatgaaaca caaacggca                                                 19

<210> SEQ ID NO 57
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 57
gctttctact caacgtctt                                                 19

<210> SEQ ID NO 58
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 58
tctctgccaa gtggcacaa                                                 19

<210> SEQ ID NO 59
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 59
ggactcagtt gttctgttt                                                 19

<210> SEQ ID NO 60
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 60
cccggccctg agaatatat                                              19

<210> SEQ ID NO 61
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 61
ccggccctga gaatatatt                                              19

<210> SEQ ID NO 62
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 62
ggtcagtgaa cagagtcaa                                              19

<210> SEQ ID NO 63
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 63
gcagaagtgg gcttgtcat                                              19

<210> SEQ ID NO 64
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 64
gcaggtgtgt ttatagcgt                                              19

<210> SEQ ID NO 65
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 65
gcgttgatgg accgttctt                                              19

<210> SEQ ID NO 66
<211> LENGTH: 19
<212> TYPE: DNA
<213> ORGANISM: Artificial Sequence
<220> FEATURE:
<223> OTHER INFORMATION: Synthetic oligonucleotide

```
<400> SEQUENCE: 66
cctgactgcg tgcatgaaa                                              19

<210> SEQ ID NO 67
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 67
gcctggacag cactgattt                                              19
```